United States Patent [19]

Tabor et al.

[11] Patent Number: 5,776,673
[45] Date of Patent: Jul. 7, 1998

[54] TREATMENT AND DETECTION OF TUBERCULOSIS, LEPROSY, AND RELATED DISEASES

[75] Inventors: Stanley Tabor, Cambridge; Charles C. Richardson, Chestnut Hill, both of Mass.

[73] Assignee: President and Fellows of Harvard College, Cambridge, Mass.

[21] Appl. No.: 427,072

[22] Filed: Apr. 21, 1995

[51] Int. Cl.$^6$ .............................. C12Q 1/68; A61K 39/40
[52] U.S. Cl. .................... 435/6; 424/168.1; 536/23.1; 536/24.1; 536/24.32; 435/91.1
[58] Field of Search ................... 424/168.1; 536/23.1, 536/24.1, 24.32; 435/6, 91.1

[56] References Cited

PUBLICATIONS

Astatike et al., "Deoxynucleoside Triphosphate amd Pyrophosphate Binding Sites in the Catalytically Competent Ternary Complex for the Polymerase Reaction Catalyzed by DNA Polymerase I (Klenow Fragment)"*J. Biol. Chem.*270:1945–1954 (1995).
Bloom and Murray, "Tuberculosis: Commentary on a Reemergent Killer,"*Science* 257:1055 (1992).
Bozzette and Richman, "Salvage Therapy for Zidovudine–Intolerant HIV–Infected Patients with Alternating and Intermittent Regimens of Zidovudine and Dideoxycytidine," *American Journal of Medicine* 88 (Supp. 5B) 5B–24S (1990).
Braithwaite and Ito, "Compilation, alignment, and phylogenetic relationships of DNA polymerases," *Nucleic Acids Research* 21:787 (1993).
Broder, "Dideoxycytidine (ddC): A Potent Antiretroviral Agent for Human Immunodeficiency Virus Infection," *American Journal of Medicine* 88 (Supp. 5B)5B–1S (1990).
Broder and Yarchoan, "Dideoxycytidine: Current Clinical Experience and Future Prospects," *American Journal of Medicine* 88 (Supp. 5B) 5B–31S (1990).
Chen and Cheng, "The Role of Cytoplasmic Deoxycytidine Kinase in the Mitochondrial Effects of the Anti–human Immunodeficiency Virus Compound, 2', 3'–Dideoxycytidine," *J. Biol. Chem*267:2856 (1992).
Cohn, *Management of Infection on HIV Disease*, 8:399 (1994).
San Sarrig, *Lepr. Rev.*65:81 (1994).
Collins, "Tuberculosis: The Return of an Old Enemy," *Crit. Rev. Micro.*19:1 (1993).
Delarue et al., "An Attempt to unify the structure of polymerases,"*Protein Engineering* 3:461–467 (1990).
Edenberg et al., "Involvement of DNA Polymerase βin Simian Virus 40 DNA Replication," *J. Biol. Chem.*258:3273 (1978).

Lipsky, "Zalcitabine and didanosine," *The Lancet* 3341:30 (1993).
Meng et al., "AIDS Clinical Trials Group: Phase I/II Study of Combination 2', 3'–Dideoxycytidine and Zidovudine in Patients with Acquired Immunodeficiency Syndrome (AIDS) and Advanced AIDS–Related Complex," *American Journal of Medicine* 88 (Supp. 5B) 5B–27S (1990).
Merigan et al., "Safety and Tolerance of Dideoxycytidine as a Single Agent," *American Journal of Medicine* 88 (Supp. 5B) 5B–11S (1990).
Mizrahi et al., "A PCR method for the sequence analysis of the gyrA, polA, and rnhA gene segments from mycobacteria," *Gene* 136:287 (1993).
Pizzo, "Treatment of Human Immunodeficiency Virus–Infected Infants and Young Children with Dideoxynucleosides," *American Journal of Medicine* 88 (Supp. 5B) 5B–16S (1990).
Richman, "Susceptibility to Nucleoside Analogues of Zidovudien–Resistant Isolates of Human Immunodeficiency Virus," *American Journal of Medicine* 88 (Supp. 5B) 5B–8S (1990).
Skowron, "Alternating and Intermittent Regimens of Zidovudine (3'–azido–3'–deoxythymidine) and Dideoxycytiudine (2', 3'–dideoxycytidine) in the Treatment of Patients with Acquired Immunodeficiency Syndrome (AIDS) and AIDS–Related Complex," *American Journal of Medicine* 88 (Supp. 5B) 5B–20S (1990).
Tabor and Richardson, "Selective Inactivation of the Exonuclease Activity of Bacteriophage T7 DNA Polymerase by in vitro Mutagenesis," *J. Biol. Chem.*264:6447 (1989).
Tabor and Richardson, "DNA Sequence Analysis with a Modified Bacteriophage T7 DNA Polymerase," *J. Biol. Chem.*265:8322 (1990).
Tabor and Richardson, "Effect of manganese ions of the incorporation of dideoxynucleotides by bacteriophage T7 DNA polymerase and *Escherichia coli* DNA polymerase I," *J. Biol. Chem.*86:4076 (1989).
Van der Vleit and Kwant, "Role of DNA polymerase y in adenovirus DNA replication," *Nature* 276:532 (1978).
Waqar et al., "Effects of 2', 3'–Dideoxynucleosides on Mammalian Cells and Viruses," *Journal of Cellular Physiology* 12:402 (1984).
Young and Cole, "Leprosy, Tuberculosis, and the New Genetics," *Journal of Bacteriology* 175:1 (1993).

*Primary Examiner*—James C. Housel
*Assistant Examiner*—Jennifer Shaver
*Attorney, Agent, or Firm*—Lyon & Lyon LLP

[57] ABSTRACT

Method for treatment of an infection in an animal or plant by an organism having a non-discriminating DNA polymerase. The organism is contacted with a therapeutically effective amount of a dideoxynucleoside or dideoxynucleotide in a pharmaceutically acceptable buffer. Such contact reduces the infection or a symptom of the infection in the animal or plant.

3 Claims, No Drawings

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: Protein ( x i ) SEQUENCE DESCRIPTION: SEQ ID NO: 1:

```
Glu  Gln  Arg  Arg  Ser  Ala  Lys  Ala  Ile  Asn  Phe  Gly  Leu  Ile  Tyr  Gly
 1                    5                          10                         15

Met  Ser  Ala  Phe  Gly  Leu  Ala  Arg  Gln  Leu  Asn  Ile
```

20                          25

( 2 ) INFORMATION FOR SEQ ID NO: 2:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: Protein ( x i ) SEQUENCE DESCRIPTION: SEQ ID NO: 2:

Leu Met Arg Arg Ala Ala Lys Thr Ile Asn Phe Gly Val Leu Tyr Gly
1               5                   10                  15

Met Ser Ala His Arg Leu Ser Gln Glu Leu Ala Ile
            20                  25

( 2 ) INFORMATION FOR SEQ ID NO: 3:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: Protein ( x i ) SEQUENCE DESCRIPTION: SEQ ID NO: 3:

Leu Met Arg Arg Ala Ala Lys Thr Val Asn Phe Gly Val Leu Tyr Gly
1               5                   10                  15

Met Ser Ala His Arg Leu Ser Gln Glu Leu Ala Ile
            20                  25

( 2 ) INFORMATION FOR SEQ ID NO: 4:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: Protein ( x i ) SEQUENCE DESCRIPTION: SEQ ID NO: 4:

Leu Met Arg Arg Ala Ala Lys Thr Ile Asn Phe Gly Val Leu Tyr Gly
1               5                   10                  15

Met Ser Ala His Arg Leu Ser Gly Glu Leu Ser Ile
            20                  25

( 2 ) INFORMATION FOR SEQ ID NO: 5:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: Protein ( x i ) SEQUENCE DESCRIPTION: SEQ ID NO: 5:

Asn Gln Arg Arg Ala Ala Lys Thr Val Asn Phe Gly Val Leu Tyr Gly
1               5                   10                  15

Met Ser Ala His Arg Leu Ser Asn Asp Leu Gly Ile
            20                  25

( 2 ) INFORMATION FOR SEQ ID NO: 6:

( i ) SEQUENCE CHARACTERISTICS:
        ( A ) LENGTH: 28 amino acids
        ( B ) TYPE: amino acid (D) TOPOLOGY: linear (ii) MOLECULE TYPE: Protein (xi) SEQUENCE DESCRIPTION: SEQ ID NO: 6:

```
Asn Asp Arg Arg Asn Ala Lys Ala Val Asn Phe Gly Val Val Tyr Gly
 1               5                  10                      15
Ile Ser Asp Phe Gly Leu Ser Asn Asn Ile Gly Ile
             20                  25
```

(2) INFORMATION FOR SEQ ID NO: 7:

(i) SEQUENCE CHARACTERISTICS:
        (A) LENGTH: 28 amino acids
        (B) TYPE: amino acid
        (D) TOPOLOGY: linear (ii) MOLECULE TYPE: Protein (xi) SEQUENCE DESCRIPTION: SEQ ID NO: 7:

```
Asn Met Arg Arg Gln Ala Lys Ala Val Asn Phe Gly Ile Val Tyr Gly
 1               5                  10                      15
Ile Ser Asp Tyr Gly Leu Ala Gln Asn Leu Asn Ile
             20                  25
```

(2) INFORMATION FOR SEQ ID NO: 8:

(i) SEQUENCE CHARACTERISTICS:
        (A) LENGTH: 28 amino acids
        (B) TYPE: amino acid
        (D) TOPOLOGY: linear (ii) MOLECULE TYPE: Protein (xi) SEQUENCE DESCRIPTION: SEQ ID NO: 8:

```
Val Pro Arg Lys Val Gly Lys Thr Ala Asn Phe Gln Lys Val Tyr Gly
 1               5                  10                      15
Gly Gly Ala Lys Ala Leu Ala Glu Ala Val Gly Ile
             20                  25
```

(2) INFORMATION FOR SEQ ID NO: 9:

(i) SEQUENCE CHARACTERISTICS:
        (A) LENGTH: 28 amino acids
        (B) TYPE: amino acid
        (D) TOPOLOGY: linear (ii) MOLECULE TYPE: Protein (xi) SEQUENCE DESCRIPTION: SEQ ID NO: 9:

```
Ala Leu Arg Gln Ala Ala Lys Ala Ile Thr Phe Gly Ile Leu Tyr Gly
 1               5                  10                      15
Ser Gly Pro Ala Lys Val Ala His Ser Val Asn Glu
             20                  25
```

(2) INFORMATION FOR SEQ ID NO: 10:

(i) SEQUENCE CHARACTERISTICS:
        (A) LENGTH: 26 amino acids
        (B) TYPE: amino acid
        (D) TOPOLOGY: linear (ii) MOLECULE TYPE: Protein (xi) SEQUENCE DESCRIPTION: SEQ ID NO: 10:

```
Asp Gln Arg Thr Ala Ser Lys Lys Ile Gln Phe Gly Ile Val Tyr Gln
 1               5                  10                      15
```

Glu Ser Ala Arg Gly Leu Ser Glu Asp Leu
            20                  25

(2) INFORMATION FOR SEQ ID NO: 11:

(i) SEQUENCE CHARACTERISTICS:
      (A) LENGTH: 28 amino acids
      (B) TYPE: amino acid
      (D) TOPOLOGY: linear (ii) MOLECULE TYPE: Protein (xi) SEQUENCE DESCRIPTION: SEQ ID NO: 11:

Pro Leu Arg Gln Lys Gly Lys Val Ala Glu Leu Ala Leu Gly Tyr Gln
1               5                   10                  15
Gly Gly Lys Gly Ala Leu Ile Gln Met Gly Ala Leu
            20                  25

(2) INFORMATION FOR SEQ ID NO: 12:

(i) SEQUENCE CHARACTERISTICS:
      (A) LENGTH: 27 amino acids
      (B) TYPE: amino acid
      (D) TOPOLOGY: linear (ii) MOLECULE TYPE: Protein (xi) SEQUENCE DESCRIPTION: SEQ ID NO: 12:

Thr Arg Asp Asn Ala Lys Thr Phe Ile Tyr Gly Phe Leu Tyr Gly Ala
1               5                   10                  15
Gly Asp Glu Lys Ile Gly Gln Ile Val Gly Ala
            20                  25

(2) INFORMATION FOR SEQ ID NO: 13:

(i) SEQUENCE CHARACTERISTICS:
      (A) LENGTH: 28 amino acids
      (B) TYPE: amino acid
      (D) TOPOLOGY: linear (ii) MOLECULE TYPE: Protein (xi) SEQUENCE DESCRIPTION: SEQ ID NO: 13:

Cys Ser Arg Asn Glu Ala Lys Ile Phe Asn Tyr Gly Arg Ile Tyr Gly
1               5                   10                  15
Ala Gly Ala Lys Phe Ala Ser Gln Leu Leu Lys Arg
            20                  25

(2) INFORMATION FOR SEQ ID NO: 14:

(i) SEQUENCE CHARACTERISTICS:
      (A) LENGTH: 28 amino acids
      (B) TYPE: amino acid
      (D) TOPOLOGY: linear (ii) MOLECULE TYPE: Protein (xi) SEQUENCE DESCRIPTION: SEQ ID NO: 14:

Glu Leu Arg Arg Arg Val Lys Ala Met Ser Tyr Gly Leu Ala Tyr Gly
1               5                   10                  15
Leu Ser Ala Tyr Gly Leu Ser Gln Gln Leu Lys Ile
            20                  25

(2) INFORMATION FOR SEQ ID NO: 15:

(i) SEQUENCE CHARACTERISTICS:

(A) LENGTH: 28 amino acids
(B) TYPE: amino acid
(D) TOPOLOGY: linear (ii) MOLECULE TYPE: Protein (xi) SEQUENCE DESCRIPTION: SEQ ID NO: 15:

Glu Leu Arg Arg Arg Val Lys Ala Met Ser Tyr Gly Leu Ala Tyr Gly
1               5                   10                  15

Leu Ser Ala Tyr Gly Leu Ala Thr Gln Leu Lys Ile
            20                  25

(2) INFORMATION FOR SEQ ID NO: 16:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO: 16:

TTTTCCCAGT CACGACGTTG TAAAACGACG GCCAGTGCCA      40

(2) INFORMATION FOR SEQ ID NO: 17:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO: 17:

GGCGACGTTG TAAAACGACG GCCAGTGCCA      30

(2) INFORMATION FOR SEQ ID NO: 18:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO: 18:

CCCCTTGGCA CTGGCCGTCG TTTACAACG TCG      33

(2) INFORMATION FOR SEQ ID NO: 19:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO: 19:

GGCGACGTTG TAAAACGACG GCCAGTGCCA      30

(2) INFORMATION FOR SEQ ID NO: 20:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO: 20:

TTTTGACTGG CACTGGCCGT CGTTTTACAA CGTCG      35

TREATMENT AND DETECTION OF TUBERCULOSIS, LEPROSY, AND RELATED DISEASES

This invention was made with U.S. government support including a grant from the DOE Contract No. DE-FG-02-88ER-60688. The U.S. government may have certain rights in the invention.

BACKGROUND OF THE INVENTION

This invention relates to treatment and diagnosis of diseases such as tuberculosis and leprosy.

The following is a brief description of art relevant to treatment of leprosy and tuberculosis techniques. This is provided only to give general guidance to those reading the application, and is not an admission that any art cited herein or referred to explicitly or implicitly is prior art to the appended claims.

Leprosy and particularly tuberculosis (TB) remain major health problems. There are about 3 million cases of leprosy worldwide, most in third world countries. There are an estimated 8 million new cases of tuberculosis each year and 3 million deaths resulting from TB. After years of decline in the rate of TB, there has been an alarming increase in the rate of deaths due to antibiotic-resistant strains. Multi-drug chemotherapy is routinely used now to reduce the chance of outgrowth of resistant strains. TB is an increasing problem worldwide because it is an opportunistic infection often associated with AIDS. In addition, it has recently been indicated to be passed from one human to another within an airplane.

Yaung and Cole 175 *J. Bacteriol* 1, 1993 reviews treatment of leprosy and tuberculosis. Other summary articles include Bloom and Murray 257 *Science* 1055, 1992; Collins 19 *Crit. Rev. Micro.* 1, 1993; Cohn 8 *Management of Infection on HIV Disease* 399, 1994; and 65 *Lepr. Rev.* 81, 1994. (All these references are hereby incorporated by reference herein.)

SUMMARY OF THE INVENTION

Applicant has determined that various diseases or conditions are caused by the presence of an organism having a DNA polymerase that does not discriminate significantly against dideoxynucleosides (compared to the naturally occurring deoxynucleosides). Applicant believes that treatment of such diseases can now be effected by use of dideoxynucleosides or dideoxynucleotides, or variants thereof. Thus, applicant has defined a new target for therapeutic attack by existing agents. Specifically, applicant has determined that at least two mycobacterial diseases may be treated by administration of such compounds because the causative mycobacteria have DNA polymerases which are particularly sensitive to such agents, and thus present a novel therapeutic target.

Thus, in a first aspect, the invention features a method for treatment of an infection in an animal or plant by an organism having a non-discriminating DNA polymerase which does not discriminate against incorporation of dideoxynucleosides compared to deoxynucleosides. The method includes contacting the organism in the animal or plant with a therapeutically effective amount of a dideoxynucleoside or a dideoxynucleotide in a pharmaceutically acceptable buffer. The amount used will reduce the infection or a symptom of the infection in the animal or plant. Such an animal is preferably not infected with an human immunodeficiency virus (HIV).

By "non-discriminating" is meant that the DNA polymerase is able to incorporate a dideoxynucleotide (ddNTP) nearly as well, or better, than a deoxynucleotide (dNTP) into a growing DNA chain. That is, the ddNTP is incorporated at a rate which is at least one tenth the rate of incorporation of a dNTP. Such rates can be measured as in the examples below, and will take into account other activities of the polymerase, such as exonuclease activities. Such DNA polymerase targets of this invention thus differ from most naturally occurring DNA polymerases which are discriminatory, i.e., incorporate dNTPs at over 100 times or even 1000 times greater a rate than a ddNTP.

The term "symptom" and "infection" are used in their art recognized manner.

Examples of useful dideoxynucleosides are well known in the art, see, for example, Lipsky 341 *The Lancet* 30, 1993; Broder, 88 (Supp. SB) *Am. J. Med.* 5B-1S, 1990; Richman, id. at 5B-8S; Merigan et al., id. at SB-11S; Pizzo, id. at 5B-16S; Skowron, id. at 5B-20S; Bozzette and Richman, id. at 5B-24S; Meng et al., id at 5B-27S; and Broder and Yarchoan, id. at 5B-31S. Generally, a dideoxynucleoside is a chemical having a sugar moiety having only hydrogen atoms at the 2 and 3' carbons, with a nucleotide base attached to the sugar moiety. Those in the art will recognize analogs as including 4, 5 or 6 carbon-containing sugars, optionally with phosphate moieties included, and with various different nucleotide bases. In addition, the sugar may be substituted at various positions, e.g., at the 2' position with methoxy or other substituents.

In preferred embodiments, the organism is a mycobacterium; e.g., *Mycobacterium tuberculosis* or *Mycobacterium leprae;* the animal or plant is also treated with another agent having a therapeutic effect for treatment of the infection; e.g., the other agent is selected from clofazamine, dapsone, rifampin, isoniazid, pyrazinamide, streptomycin, ethambutol, and thiacetazone; and the DNA polymerase is of the polI-type and has tyrosine at a position analogous to position 762 in *E. coli* DNA polymerase I; e.g., those polymerases present in Mycobacteria, see, Astatike et al., 270 *J. Biol. Chem.* 1945, 1995; Mizraki et al., 136 *Gene* 287, 1993, and associated sequences with Genbank Accession No. U00021 and L11920 (all hereby incorporated by reference herein).

Thus, in a related aspect, the invention features treatment as described above for organisms having a DNA Pol I-type enzyme which has a tyrosine at the position analogous to 762 in *E. coli* DNA Pol I. By "analogous" is meant the position in the polymerase which is responsible for discrimination between ddNTPs and dNTPs.

In another related aspect, the invention features a method for screening for a compound useful for treatment of an infection in an animal or plant by an organism as described above. The method includes determining whether a potential compound is incorporated into a growing DNA chain by a non-discriminating DNA polymerase and is not incorporated to as great a degree by a discriminating DNA polymerase. In preferred embodiments, the compound is a nucleoside or nucleotide analog.

By "as great an extent" is meant that the compound is incorporated by a discriminatory DNA polymerase at least 100 fold less than by the non-discriminatory DNA polymerase. In this way, such an agent will specifically target organisms having such non-discriminatory DNA polymerases, and leave other organisms or cells, without such polymerases, unaffected.

In another related aspect, the invention features a pharmaceutical composition for treatment of an infection in an animal or plant by an organism having a non-discriminating DNA polymerase (except for an animal infected with an human immunodeficiency virus). The composition includes a therapeutically effective amount of an agent which is incorporated into a growing DNA chain by a non-discriminating DNA polymerase but is not incorporated to as great a degree by a discriminating DNA polymerase in a pharmaceutically acceptable buffer. In preferred embodiments, the therapeutically effective amount is effective for treatment of tuberculosis caused by *M. tuberculosis*, or is effective for treatment of leprosy by *M. leprae*.

In another aspect, the invention features a diagnostic method for detection of infection by an organism having a non-discriminating DNA polymerase by detection of that DNA polymerase. This detection can be performed by routine procedure, e.g., by detection of the polymerase activity itself (e.g., as shown below), by Northern or Southern blots using oligonucleotides specific for a polymerase-encoding RNA or DNA, by use of specific antibodies, or by DNA sequence analysis after amplification by PCR.

Other features and advantages of the invention will be apparent from the following description of the preferred embodiments thereof, and from the claims.

DESCRIPTION OF THE PREFERRED EMBODIMENTS

Applicant exemplifies the present invention by treatment of two diseases characterized by the presence of a non-discriminating DNA polymerase. Those in the art will recognize that other organisms which create disease in an animal or plant can be readily identified by determining the presence of a non-discriminating DNA polymerase as shown in the examples below. These examples are taken from Tabor and Richardson, U.S. Ser. No. 08/337,615 hereby incorporated by reference herein. Thus, by routine procedures other DNA polymerases which do not discriminate against incorporation of dideoxynucleotides can be defined. The organism containing such a DNA polymerase will therefore be potentially susceptible to treatment by use of dideoxynucleosides or analogs thereof. The examples of treatment of leprosy and tuberculosis are thus not limiting in the invention, and will be recognized as such by those in the art.

The DNA polymerase targets of this invention do not discriminate significantly between incorporation of dideoxynucleotide analogs and deoxynucleotides along the length of the DNA template. That is, these polymerases are unable to discriminate significantly between a nucleotide that has a 3' hydroxyl group versus one that does not (i.e., has two hydrogens at the 3' position of the ribose). However, these polymerases may discriminate against modifications at other positions on the nucleosides. For example, the polymerases may discriminate against some dideoxynucleotide analogs which have fluorescent groups attached compared to deoxynucleotides. Such non-discriminating polymerases are sensitive to dideoxynucleotides. See, Edenberg et al., 253 *J. Biol. Chem.* 3273, 1978; Wagner et al., 121 *J. Cell Physiol.* 121, 1984; Van der Vleit and Kwant, 276 *Nature* 532, 1978; and Chen and Cheng, 267 *J. Biol. Chem* 2856, 1992 (all hereby incorporated by reference herein).

Thus, the DNA polymerase targets of this invention provide a uniform efficiency of incorporation of chain terminating agents (of which a ddNTP is an example, and is commonly used for DNA sequencing as described by Tabor and Richardson, supra), even if they discriminate against overall incorporation. In addition, other DNA polymerase targets of this invention will give a more uniform incorporation with fluorescent ddNTPs than the corresponding enzyme in other organisms, although not as uniform as with unmodified ddNTPs.

Those in the art can use routine methods (exemplified below) to determine those polymerases which are non-discriminating, and thus are useful targets of this invention.

Specific Polymerases

To exemplify the breadth of the invention the following polymerases are described which define various DNA Pol I and Pol II targets. Of these enzymes those in the art will recognize that many are discriminating polymerases with no value in this invention as targets. See Braithwaite and Ito, 21 *Nucleic Acids Research* 787, 1993.

1. Pol I family

These include: *E. coli* DNA polymerase I, *Streptococcus pneumoniae* DNA polymerase I, *Thermus aguaticus* DNA polymerase I, *Thermus flavus* DNA polymerase I, Bacteriophage T5 DNA polymerase, Bacteriophage SPO1 DNA polymerase, Bacteriophage SPO2 DNA polymerase, *Mycobacterium tuberculosis*, DNA polymerase I, *Mycobacterium leprae* DNA polymerase I and Mitochondrial DNA polymerase.

2. Polymerase alpha family (also called polymerase II family)

Delarue et al., *Protein Engineering* 3, 461–467 (1990) show that the two families of polymerases (polymerase I family and polymerase alpha family) share three common motifs. The region they call "Motif B" contains the residue we have identified as responsible for specificity for the dideoxyribose moiety. This region is characterized by the sequence K $N_1$ $N_2$ $N_3$ $N_4$ $N_5$ N6 $N_7$ Y G in the polymerase I family, where $N_4$ is the specificity residue: if $N_4$ is a phenylalanine there is high discrimination, if $N_4$ is tyrosine there is low discrimination. In the polymerase alpha family, the sequence is K $N_1$ $N_2$ $N_3$ $N_4$ $N_5$ $N_6$ Y G (there is one less base between the conserved residues). We predict therefore that just as with polymerase I type enzymes, the presence of a different residue(s) in this motif (between the lysine (K) and the tyrosine (Y)) will reduce the discrimination of these polymerases to ddNTPs.

These enzymes include: *Escherichia coli* DNA polymerase II, PRD1 DNA polymerase, Ø 29 DNA polymerase, M2 DNA polymerase, T4 DNA polymerase, *Thermuococcus litoralis* DNA polymerase (Vent), *Pyrococcus furiosus* DNA polymerase, *Sulfolobus solfataricus* DNA polymerase, Human DNA polymerase alpha, *S. cerevisiae* DNA polymerase I (alpha), *S. pombe* DNA polymerase I (alpha), *Drosophila melanogaster* DNA polymerase alpha, *Trypanosoma brucei* DNA polymerase alpha, Human DNA polymerase delta, Bovine DNA polymerase delta, *S. cerevisiae* DNA polymerase III (delta), *S. pombe* DNA polymerase III (delta), *Plasmodium falciparum* DNA polymerase delta, *S. cerevisiae* DNA polymerase II (epsilon), *S. cerevisiae* DNA polymerase Rev3, Herpes Simplex virus type 1 DNA polymerase, Equine herpes virus type 1 DNA polymerase, Varicella-Zoster virus DNA polymerase, Epstein-Barr virus DNA polymerase, *Herpesvirus saimiri* DNA polymerase, Human cytomegalovirus DNA polymerase, Murine cytomegalovirus DNA polymerase, Human herpes virus type 6 DNA polymerase, Channel Catfish virus DNA polymerase, Chlorella virus DNA polymerase, Fowlpox virus DNA polymerase, Vaccinia virus DNA polymerase, *Choristoneura biennis* DNA polymerase, *Autographa californica* nuclear polyhedrosis, virus (AcMNPV) DNA polymerase, Lymantria dispar nuclear polyhedrosis virus, DNA polymerase, Adenovirus-2 DNA polymerase, Adenovirus-7

DNA polymerase, Adenovirus-12 DNA polymerase, S-1 maize DNA polymerase, *kalilo neurospora intermedia* DNA polymerase, AI2 *Ascobolus immersus* DNA polymerase, pCLK1 *Claviceps purpurea* DNA polymerase, *Maranhar neurospora crassa* DNA polymerase, pEM *Agaricus bitorguis* DNA polymerase, pGKL1 *Kluyveromyces lactis* DNA polymerase, pGKL2 *Kluyveromyces lactis* DNA polymerase, and pSKL *Saccaromyces kluyveri* DNA polymerase.

Some of the DNA polymerases of interest belong to the family referred to as "Pol I-type" DNA polymerases, named for the fact that they all share extensive homology to *E. coli* DNA polymerase I. The genes of 15 Pol I-type DNA polymerases have been sequenced. The deduced amino acid sequence of the relevant region of these polymerases is shown in Tables I and II.

otides (and thus in their sensitivity to these chain terminating compounds). This is summarized in Table II. To date, it has been demonstrated for four different Pol I-type DNA polymerases that when each contains a phenylalanine at this critical site it discriminates 600–8,000 fold against dideoxynucleotides, and thus is not sensitive to these analogs. To date, there are also four examples of Pol I-type DNA polymerases in which it has been demonstrated that when each has a tyrosine at the critical residue it discriminates less than 10-fold against dideoxynucleotides, and thus is very sensitive to these analogs. In three examples, applicant has demonstrated that changing this single residue from tyrosine to phenylalanine or vise versa alters by more than 1,000 fold the ability of that DNA polymerase to distinguish between a deoxy- and a dideoxynucleotide. These data strongly suggest that this will be a universal effect for all Pol I-type DNA

TABLE I

Helix O Region in PolI-Type DNA Polymerases
(using standard one letter amino acid code)

| | |
|---|---|
| *Escherichia coli* | EQRRSAKAINFGLIYGMSAFGLARQLNI (SEQ ID NO.1) |
| *Thermus aquaticus* | LMRRAAKTINFGVLYGMSAHRLSQELAI (SEQ. ID. NO.2) |
| *Thermus thermophilus* | LMRRAAKTVNFGVLYGMSAHRLSQELAI (SEQ. ID. NO.3) |
| *Thermus flavus* | LMRRAAKTINFGVLYGMSAHRLSGELSI (SEQ. ID. NO.4) |
| *Deinococcus radiodurans* | NQRRAAKTVNFGVLYGMSAHRLSNDLGI (SEQ. ID. NO.5) |
| *Streptococcus pneumoniae* | NDRRNAKAVNFGVVYGISDFGLSNNIGI (SEQ. ID. NO.6) |
| *Bacillus caldotenax* | NMRRQAKAVNFGIVYGISDYGLAQNLNI (SEQ. ID. NO.7) |
| Mycobacteriophage L5 | VPRKVGKTANFQKVYGGGAKALAEAVGI (SEQ. ID. NO.8) |
| Bacteriophage T5 | ALRQAAKAITFGILYGSGPAKVAHSVNE (SEQ. ID. NO.9) |
| Bacteriophage SPO1 | DQRTASKKIQFGIVYQES.AR.GLSEDL (SEQ. ID. NO.10) |
| Bacteriophage SPO2 | PLRQKGKVAELALGYQGGKGALIQMGAL (SEQ. ID. NO.11) |
| Bacteriophage T7 | T.RDNAKTFIYGFLYGAGDEKIGQIVGA (SEQ. ID. NO.12) |
| Mitochondria (DNA polymerase τ) | CSRNEAKIFNYGRIYGAGAKFASQLLKR (SEQ. ID. NO.13) |
| *Mycobacterium tuberculosis* | ELRRRVKAMSYGLAYGLSAYGLSQQLKI (SEQ. ID. NO.14) |
| *Mycobacterium leprae* | ELRRRVKAMSYGLAYGLSAYGLATQLKI (SEQ. ID. NO.15) |

TABLE II

Summary of Ribose Selectivity Residue in Pol I-Type DNA Polymerases

| Polymerase | Residue | dNMP/ddNMP Incorporation Rate |
|---|---|---|
| *Escherichia coli* | Phenylalanine | 600 (0.6 for Phenylalanine → Tyrosine Mutant) |
| *Thermus aquaticus* | Phenylalanine | 3,000 (0.5 for Phenylalanine → Tyrosine Mutant) |
| *Thermus thermophilus* | Phenylalanine | >1,000 |
| *Thermus flavus* | Phenylalanine | |
| *Deinococcus radiodurans* | Phenylalanine | |
| *Streptococcus pneumoniae* | Phenylalanine | |
| *Bacillus caldotenax* | Phenylalanine | |
| Mycobacteriophage L5 | Phenylalanine | |
| Bacteriophage T5 | Phenylalanine | |
| Bacteriophage SPO1 | Phenylalanine | |
| Bacteriophage SPO2 | Leucine | |
| Bacteriophage T7 | Tyrosine | 3 (8,000 for Tyrosine → Phenylalanine Mutant) |
| Mitochondria | Tyrosine | <10 |
| *Mycobacterium tuberculosis* | Tyrosine | |
| *Mycobacterium leprae* | Tyrosine | |

All the known Pol I-type DNA polymerases are either from bacteria, bacteriophage, or mitochondria. All except one have a phenylalanine or tyrosine at the site recognized by Tabor and Richardson as important for ribose discrimination (see U.S. Ser. No. 08/337,615, hereby incorporated by reference herein). In the one exception (the DNA polymerase from bacteriophage SPO2) a leucine is present at this site; this DNA polymerase was initially not thought to be related to this family.

Pol I-type DNA polymerases vary tremendously in their ability to use dideoxynucleotides relative to deoxynuclepolymerases that have either a phenylalanine or tyrosine at this critical site.

All of the known bacteria with the exception of the mycobacteria (discussed below) have a DNA polymerase with phenylalanine at the critical site, and thus are not sensitive to dideoxynucleosides. This may be an evolutionary adaption to prevent the incorporation of rare, naturally occurring chain terminating analogs into the bacterial DNA, which would likely be lethal to the cell. For example, *E. coli* is normally resistant to dideoxynucleosides, because *E. coli* DNA polymerase I, that has a phenylalanine at the critical site, discriminates strongly against the incorporation of dideoxynucleotides into DNA. Applicant has placed the *E. coli* DNA polymerase I mutant gene in which the phenylalanine has been changed to tyrosine (that does not discriminate against dideoxynucleotides) back into the *E. coli* chromosome. As a consequence, these *E. coli* cells are now about 50–100 times more sensitive to dideoxynucleosides in the media compared with wild-type *E. coli*. This demonstrates that the ability of the cell's DNA polymerase I to discriminate against dideoxynucleosides is critical for the survival of the cells when these analogs are present in their environment.

There are four presently known Pol I-type DNA polymerases that naturally contain a tyrosine at the critical position. These are the DNA polymerases from bacteriophage T7, mitochondria, *Mycobacterium tuberculosis* and *Mycobacterium leprae*. These will be discussed briefly:

T7 DNA polymerase

T7 DNA polymerase incorporates dideoxynucleosides efficiently; this is the principal reason it has become widely used for DNA sequencing. Changing the tyrosine at the critical residue to phenylalanine results in a 2,500-fold increase in discrimination against ddNTPs. In vivo, the growth of phage T7 is normally sensitive to the presence of dideoxynucleosides in the media; when the critical tyrosine codon in the gene for T7 DNA polymerase is changed to a phenylalanine codon in the phage, the phage are resistant to high levels of dideoxynucleosides.

Mitochondria DNA polymerase

It has been known for nearly 20 years that the mitochondria DNA polymerase is sensitive to dideoxynucleotides, in contrast to the eucaryotic DNA polymerases responsible for eucaryotic DNA replication (DNA polymerases α and δ). It has also been known for about 15 years that reverse transcriptases are sensitive to dideoxynucleosides. This differential sensitivity to dideoxynucleosides by the HIV reverse transcriptase compared with the DNA polymerases responsible for the replication of the eucaryotic chromosomes is the mechanism by which AZT, ddI and ddC are effective chemotherapies against AIDS. However, these compounds are toxic at high doses. It is thought that this is due to their interference with mitochondrial DNA replication as a consequence of the inability of the mitochondrial DNA polymerase to discriminate against their incorporation into mitochondria DNA. This results in depletion of mitochondria in the cells. Many of the studies on the use of these drugs in AIDS patients have focused on determining the doses of each that patients can tolerate when given either individually or more commonly in combination with one another. This example demonstrates the clinical importance of the sensitivity of the different DNA polymerases in humans to dideoxynucleosides in the current use of these drugs as therapeutic agents.

Mycobacterium DNA polymerase I

The other two Pol I-type DNA polymerases with tyrosine at the critical site are the DNA polymerases from *Mycobacterium tuberculosis* and *Mycobacterium leprae*. The sequences of these two genes has been published; the gene for *M. tuberculosis* in 1993 and the gene for *M. leprae* in 1994 (see, supra). In light of the discussion above, the DNA polymerases from these two mycobacterium are probably sensitive to dideoxynucleosides. This presents the possibility that these two organisms, the causative agents of tuberculosis and leprosy, may be sensitive to treatment with dideoxynucleosides as well. If dideoxynucleosides are effective against these organisms, they will be very useful as a new antibiotic to which resistant strains have not been selected previously.

There is a history of treating AIDS patients with dideoxynucleosides. Thus, many AIDS patients that have TB have been given dideoxynucleosides for therapy. However, in these cases the dideoxynucleosides were given to combat the HIV, not the tuberculosis. It is generally assumed that ddI and ddC are anti-retroviral agents, not antibacterial. It appears that all the studies that have been carried out on the efficacy of ddI and ddC in AIDS patients focused of improvements in the patients' immune system, and that any correlation with effects on opportunistic infections such as TB were regarded as an indirect effect of improvement in the immunocompetency of the patient.

It is possible that *M. tuberculosis* and *M. leprae* may be resistant to dideoxynucleosides despite the fact that their polymerases are sensitive to these analogs. For example, mycobacteria are unusual in that most grow very slowly; *M. tuberculosis* has a doubling time of 24 hr., while *M. leprae* has a doubling time of two weeks. This is in contrast to *E. coli* which has a doubling time of 20 min. In addition, mycobacterium have a thick lipid coat that make them impervious to compounds that can enter other bacteria. Thus, it is possible dideoxynucleosides will not be able to get into these organisms, or the slow metabolism of the organisms will allow degradative enzymes to break down the dideoxynucleosides before they can be incorporated, or the slow rate of growth could allow repair processes to remove incorporated chain terminating analogs before they cause cell death. Also, it is clear that even if these organisms are sensitive to dideoxynucleosides, with time resistant strains will readily develop by mutation of the DNA polymerase, for example by modification of the critical tyrosine to phenylalanine. If this is the case then routine screens can be used to find useful analogs of dideoxynucleosides that can be used for treatment of these diseases.

EXAMPLES

Example 1. Gel electrophoresis-based determination of the rate of incorporation of dideoxynucleotides relative to deoxynucleotides using a 1:1 ratio of dNTPs to ddNTPs.

The primary application of this test is to determine the absolute ratio of incorporation of a ddNMP to a dNMP for a DNA polymerase that efficiently incorporates dideoxynucleotides, such as T7 DNA polymerase, *E. coli* DNA polymerase I mutant F762Y or Taq DNA polymerase mutant F667Y. It can also indicate the level of discrimination against ddNTPs of any DNA polymerase; however, for DNA polymerases that discriminate strongly against ddNTPs, such as T7 DNA polymerase mutant Y526F, *E. coli* DNA polymerase I or Taq DNA polymerase, higher ratios of ddNTP to dNTP are necessary to determine precisely their level of discrimination, which is described in detail in Example 2. This test is suitable for screening for useful target DNA polymerases of this invention.

DNA synthesis reactions are carried out on the $^{32}$P-end labeled 40 mer-M13 (5'd(TTTTCCCAGTCACGACGTT-GTAAAACGACGGCCAGTGCCA 3') mGP1-2 DNA template complex prepared by standard procedure (see Tabor and Richardson, supra). Reaction conditions are used that are optimum for the DNA polymerase being tested with regard to buffer, pH, salts, and temperature of the reaction. A concentration of DNA polymerase is chosen whereby most of the primers are extended in a 10 min reaction and are terminated by the incorporation of a dideoxynucleotide. The reaction mixture contains 100 μM 4dNTPs and 100 μM of one of the four ddNTPs.

We used this test to compare the ability of six DNA polymerases to incorporate each of the four ddNMPs. The DNA polymerases tested were (1) T7 DNA polymerase with a 28 amino acid deletion in the exonuclease domain and complexed in a one-to-one ratio with thioredoxin (Tabor and Richardson 264 *J. Biol. Chem.* 6447, 1989) (referred to here as "T7 DNA polymerase"), (2) The large fragment of *E. coli* DNA polymerase I, commonly called the Klenow fragment (referred to here as "*E. coli* DNA polymerase I"), (3) Unmodified DNA polymerase from *Thermus aquaticus* (referred to here as "Taq DNA polymerase"), (4) T7 DNA polymerase as described above in which the tyrosine at residue 526 has been changed to a phenylalanine (referred to here as "T7 DNA polymerase Y526F"), (5) *E. coli* DNA polymerase I as described above in which the phenylalanine at residue 762 has been changed to a tyrosine (referred to here as "*E. coli* DNA polymerase I F762Y"), and (6) Taq DNA polymerase as described above in which the phenylalanine at residue 667 has been changed to a tyrosine (referred to here as "Taq DNA polymerase F667Y").

To test the relative rate of use of each of the four ddNTPs compared to the comparable dNTPs for each of the DNA polymerases indicated above, the reaction mixtures (8 μl) contained 1.0 μl annealed $^{32}$P-labeled primer-M13 DNA as described above (~0.015 pmoles, ~200,000 cpm), 40 mM Tris.HCl, pH 8.0, 5 mM MgCl$_2$, 5 mM dithiothreitol, 50 mM NaCl, 100 μM 4dNTPs, and 100 μM ddCTP. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The reactions were initiated by the addition of 2 μl of each DNA polymerase, diluted in 20 mM Tris.HCl, pH 7.5, 10 mM 2-mercaptoethanol and 0.05% bovine serum albumin to a concentration of approximately 0.025 units/μl. The concentration of each DNA polymerase was sufficient to extend most of the labeled primers by more than 500 nucleotides in the absence of ddNTPs in a 15 min reaction. The reaction mixtures were incubated for 15 min at either 37° C. (T7 DNA polymerase, T7 DNA polymerase Y526F, *E. coli* DNA polymerase I, and *E. coli* DNA polymerase I F762Y) or 70° C. (Taq DNA polymerase and Taq DNA polymerase F667Y). The reactions were terminated by the addition of 10 μl 90% formamide, 20 mM EDTA, 0.05% bromphenol blue. Each sample was heated at 90° C. for 2 min immediately prior to loading 6 μl of each sample onto a gel consisting of 8% polyacrylamide, 0.4% N,N'-methylenebisacrylamide, 7M urea in 100 mM Tris borate, pH 8.3, 1 mM EDTA. Electrophoresis was at 2000 Volts for 90 min (until the bromphenol blue had just run off the bottom of the gel). After electrophoresis, the gel was dried under vacuum, and autoradiographed. After autoradiography, the distribution of radioactively labeled fragments was determined by Phosphorimager analysis (Molecular Dynamics). Alternatively, the relative intensities of dideoxy-terminated bands can be determined by scanning the autoradiograph using an instrument such as the SciScan 5000 imaging densitometer (United States Biochemical Corp).

When the set of four reactions (each containing a single ddNTP at an equimolar concentration as the dNTP) was carried out with each of the six DNA polymerases described above, the reactions with three of the DNA polymerases (T7 DNA polymerase Y526F, *E. coli* DNA polymerase I and Taq DNA polymerase) resulted in most (>50%) of the radioactivity in the primers that had been extended migrating at the top of the gel, corresponding to fragments greater than 300 bases in length. Based on the predicted exponential decay of signal with increasing fragment size, this corresponds to discrimination by these three DNA polymerases of more than 100 fold against all four ddNTPs. A more precise measurement of the discrimination against ddNTPs by these three DNA polymerases is obtained using the test in Example 2 below.

For the other three DNA polymerases (T7 DNA polymerase, *E. coli* DNA polymerase I F762Y and Taq DNA polymerase F667Y) the autoradiograph showed a series of dideoxy-terminated fragments with all of the reactions. In general, the average lengths of the labeled synthesized fragments were lowest for Taq DNA polymerase F667Y, with only about six radioactively labeled dideoxy-terminated fragments visible with even a several day exposure of the film. The average lengths of labeled fragments with *E. coli* DNA polymerase I F762Y are slightly longer than with Taq DNA polymerase F667Y, while the average lengths are significantly longer with T7 DNA polymerase. The fragments are more uniform in intensity when synthesized by *E. coli* DNA polymerase I F762Y and Taq DNA polymerase F667Y that by T7 DNA polymerase.

The distribution of radioactivity in the fragments was quantitated by Phosphoimager analysis (Molecular Dynamics). The total amount of labeled primers in each lane was determined by running three control reactions in which no DNA polymerase was present, and the radioactivity in each of the corresponding radioactive bands on the gel at the position of the unextended primer was determined. With some preparations of radioactively labeled primers, a certain percentage (<10%) is not extended by any of the DNA polymerases, regardless of the concentration of DNA polymerase used; this background level is determined by measuring the percentage of radioactivity remaining at the position of unextended primer for a series of four reactions containing ddNTPs, and subtracting the average of these four values from the total number of counts determined previously. This value is defined as the total number of counts in primers that are capable of being extended by a DNA polymerase.

The total number of counts (i.e., radioactivity) in the first three dideoxy-terminated fragments were determined for T7 DNA polymerase, *E. coli* DNA polymerase I F762Y and Taq DNA polymerase F667Y for each of the four ddNTP reactions. The values are presented in the Table below as the percentage of counts in the first three dideoxy-terminated fragments to the total number of counts in the primers capable of being extended by a DNA polymerase.

| Polymerase | Reaction | | | |
| --- | --- | --- | --- | --- |
| | ddGTP | ddATP | ddTTP | ddCTP |
| T7 DNA Polymerase | 67% | 66% | 76% | 61% |
| E. coli DNA Polymerase I F762Y | 95% | 92% | 96% | 92% |
| Taq DNA Polymerase F667Y | 97% | 95% | 95% | 99% |

As a further test of the efficiency of each DNA polymerase to incorporate dideoxynucleotides, the number of counts in each fragment with a significant signal was determined for each reaction, and the data were plotted as a function of the fragment number using the Macintosh program Kaleidograph Version 3.0 (Synergy Software). The resulting plots were fit to an exponential decay curve using the Kaleidograph library routine for this function. The decay curve is given by the equation:

$$Y = e^{M*X}$$

where:

Y=1—(the fraction of labeled primers in fragments 1 to X compared to the total number of primers that can be extended)

X=the fragment number (the first dideoxy-terminated fragment is 1)

M=the exponential decay function calculated for the data by the standard Kaleidograph library routine.

In the Table below, the following data are provided for each of the four ddNTP reactions using T7 DNA polymerase, E. coli DNA polymerase I F762Y and Taq DNA polymerase F667Y:

N, the number of fragments used to fit each exponential curve.

M, the calculated exponential decay function as described above.

D, the discrimination factor given as the ratio of the use of a specific DNTP to the use of the comparable ddNTP when both nucleotides are present at equal concentrations. D is calculated from the equation above using the calculated value of M to determine Y when X=1, and defining D, the ratio of preference of the dNTP to the ddNTP, as Y/(1−Y).

$R^2$, the correlation index for the data, was calculated by the Kaleidograph library routine. This is a measure of the variability in band intensities, or the sequence-specific variability in the ability of a DNA polymerase to incorporate the specific dideoxynucleotide.

| Polymerase | ddNTP | N | M | D | $R^2$ |
|---|---|---|---|---|---|
| T7 DNA | ddGTP | 8 | −0.375 | 2.2 | 0.813 |
| polymerase | ddATP | 6 | −0.356 | 2.3 | 0.996 |
| | ddTTP | 5 | −0.450 | 1.8 | 0.997 |
| | ddCTP | 8 | −0.317 | 2.7 | 0.889 |
| E. coli DNA | ddGTP | 5 | −1.03 | 0.56 | 0.999 |
| polymerase I | ddATP | 5 | −0.860 | 0.72 | 0.998 |
| F762Y | ddTTP | 5 | −1.06 | 0.54 | 1.000 |
| | ddCTP | 6 | −0.842 | 0.75 | 1.000 |
| Taq DNA | ddGTP | 5 | −1.18 | 0.45 | 0.995 |
| polymerase | ddATP | 6 | −0.997 | 0.59 | 0.997 |
| F667Y | ddTTP | 6 | −1.01 | 0.56 | 0.996 |
| | ddCTP | 4 | −1.44 | 0.32 | 0.996 |
| Averages: | | | | | |
| T7 DNA polymerase | 4 ddNTP | | | 2.3 | .924 |
| E. coli DNA polymerase I F762Y | 4 ddNTP | | | 0.64 | .999 |
| Taq DNA polymerase F667Y | 4 ddNTP | | | 0.48 | .996 |

In summary, T7 DNA polymerase discriminates an average of 2.3 fold against ddNTPs, while E. coli DNA polymerase I F762Y and Taq DNA polymerase F667Y actually prefer ddNTPs over dNTPs an average of 1.6 fold (1/0.64) and 2.1 fold (1/0.48), respectively. A comparison of $R^2$ indicates that the intensity of neighboring fragments are more uniform with E. coli DNA polymerase I F762Y and Taq DNA polymerase F667Y than with T7 DNA polymerase. For a more accurate measure of uniformity, a greater number of fragments could be included in the analysis by reducing the level of ddNTPs (for example by 5 fold) in each reaction, reducing the decay in intensity at each position (see Example 2).

To determine the amount of discrimination against ddNTPs by a new DNA polymerase, reactions analogous to those described above would be carried out, and identical reactions would be carried out in parallel using T7 DNA polymerase (SEQUENASE Version 2.0, United States Biochemical Corporation), with all reactions analyzed on the same gel. An initial comparison of the distribution of dideoxy-terminated bands obtained with the new DNA polymerase compared with those obtained with T7 DNA polymerase would indicate whether the new DNA polymerase discriminated more or less against ddNTPs than T7 DNA polymerase. For example, such a visual inspection using E. coli DNA polymerase I F762Y clearly shows that for reactions with each of the 4 ddNTPs, the number of fragments visible on the gel in reactions using E. coli DNA polymerase I F762Y are less (and smaller in average size) than those using T7 DNA polymerase. A more quantitative analysis could then be carried out analogous to that described above in order to calculate the exponential decay factor (M), average relative rate of utilization of dNTPs relative to dNTPs (D) and variability in intensity ($R^2$) for the new DNA polymerase as described above.

One complication that can occur in this test is when the DNA polymerase has an associated exonuclease activity, such as the 5' to 3' exonuclease activity associated with Taq DNA polymerase and the 3' to 5' exonuclease activity associated with E. coli DNA polymerase I and native T7 DNA polymerase (not the Δ28 T7 DNA polymerase deletion mutant used in the experiments above). A 5' to 3' exonuclease activity is detrimental since it can remove the label on the 5' end of the primer, reducing the radioactivity signal being detected. This problem can be partially avoided by reducing the amount of DNA polymerase in the reaction mixture. In the example above, 0.025 units of Taq DNA polymerase resulted in virtually all of the primers being extended until terminated by incorporation of a dideoxynucleotide, without appreciable loss in radioactivity due to 5' to 3' exonuclease activity, whereas a 40 fold increase in Taq DNA polymerase activity, or 1 unit per reaction, resulted in the loss of virtually all $^{32}$P from the 5' ends of the primer. An alternative approach to measuring the extent of discrimination for a DNA polymerase with a 5' to 3' exonuclease activity is to use a different assay such as those described in Examples 3–5.

A 3' to 5' exonuclease activity can complicate the assay described above by making the DNA polymerase appear to discriminate more against a ddNTP than it actually does (for example, see Tabor and Richardson, 86 Proc. Natl. Acad. Sci. 4076, 1987). This is because once a dideoxynucleotide has been incorporated, the exonuclease activity can preferentially remove the dideoxynucleotide so that DNA synthesis can continue, resulting in an increase in the length of the fragment. Preferably, the enzymes assayed in the test described above are devoid of such 3' to 5' exonuclease activity; examples are modified T7 DNA polymerase (Sequenase®, United States Biochemical Corporation), Taq DNA polymerase, exonuclease-deficient Vent (Thermococcus litoralis) DNA polymerase (New England Biolabs catalog number 257), exonuclease-deficient Deep Vent (Pyrococcus GB-1) DNA polymerase (New England Biolabs catalog number 259), exonuclease-deficient Pfu (*Pyrococcus furiosus*) DNA polymerase (Stratagene catalog number 600163), and exonuclease-deficient Klenow fragment (*E. coli* DNA polymerase I, United States Biochemical Corporation, catalog number 70057). In some instances, such as with *E. coli* DNA polymerase I (Klenow fragment) the 3' to 5' exonuclease activity is weak and does not interfere significantly with this assay (see for example Tabor and Richardson 264 *J. Biol. Chem.* 6447, 1989). One method to determine whether a new DNA polymerase being tested has a 3' to 5' exonuclease activity that is interfering with the ability to accurately measure the discrimination against ddNTPs is to carry out the experiment described above, removing aliquots at different time points up to 60 min. If the size distribution of the dideoxy-terminated fragments increases with time, then it is likely that such a 3' to 5' exonuclease activity is interfering with the assay, while if the distribution of fragments is constant over time then such an activity is not having a significant effect. If the average fragment length is increasing with time, then one should use a shorter incubation time and/or decrease the DNA polymerase concentration to a range in which the fragment sizes remain constant with time.

Pyrophosphorolysis, or the reversal of the polymerase reaction, can have a similar effect as the 3' to 5' exonuclease activity, allowing the DNA polymerase to remove the chain terminating dideoxynucleotide and further increase the length of the fragments (see Tabor and Richardson, 265 *J. Biol. Chem.* 8322, 1990). This activity is readily avoided by including pyrophosphatase in the reaction mixture, in order to remove the pyrophosphate that accumulates during DNA synthesis and is a necessary substrate for pyrophosphorolysis.

Example 2. Gel electrophoresis-based determination of the rate of incorporation of dideoxynucleotides relative to deoxynucleotides by varying the ratio of dNTPs to ddNTPs.

This example is similar to that described in Example 1. While it is the preferred test for DNA polymerases that discriminate strongly against the incorporation of dideoxynucleotides (e.g. T7 DNA polymerase Y526F, *E. coli* DNA polymerase I and Taq DNA polymerase), it also works well with DNA polymerases that efficiently incorporate ddNMPs (e.g. T7 DNA polymerase, *E. coli* DNA polymerase I mutant F762Y and Taq DNA polymerase mutant F667Y). In this test, the ratio of ddNTP to dNTP is varied for two different DNA polymerase preparations, keeping all other aspects of the reactions identical, and the distributions of dideoxy-terminated radioactively labeled fragments are compared to determine the ratios required for the two DNA polymerases being tested to obtain fragments of comparable average length.

The average length of a series of fragments is determined in one of two ways. In the first, which is best for DNA polymerases that incorporate ddNMPs efficiently, one inspects the autoradiograph and determines the position of the largest fragments visible on a given exposure for a series of reactions containing ddNTP:dNTP ratios that vary by two-fold increments using one DNA polymerase, and compares that to an analogous series using the second DNA polymerase, to determine the ratios required to generate fragments of comparable size for the two DNA polymerases. The position of the front marking the appearance of visible radioactive bands is usually relatively sharp and readily observed by eye. However, it is also possible to determine such positions more precisely using the Phosphoimager to locate the position in each lane where a certain threshold of radioactivity per unit area occurs, starting at the top of the gel and moving down the gel.

Some DNA polymerases discriminate very strongly against the incorporation of dideoxynucleotides, in which case it is difficult to add sufficient ddNTPs to the reaction to clearly detect the position of the largest dideoxy-terminated fragments on a denaturing polyacrylamide gel. For such DNA polymerases, one can use an alkaline agarose gel electrophoresis to compare the lengths of the dideoxy-terminated fragments in the different series. If one uses a denaturing polyacrylamide gel, then an alternative method to determine the ratios of ddNTP:dNTP required for the two DNA polymerases to generate dideoxy-terminated fragments of comparable average lengths is to focus on one or several bands and determine the ratio of ddNTPs to dNTPs required to obtain a specific level of radioactivity in those fragments, as analyzed by the Phosphoimager, for the two DNA polymerases being tested.

These tests were carried out using the six DNA polymerases described in Example 1. The reaction conditions were identical to that described in Example 1 except for the concentrations of dNTPs and ddNTPs. All reaction mixtures contained 10 µM 4 dNTPs. Each of the four ddNTP concentrations were varied by two-fold increments in the following ranges for the six DNA polymerases as follows: T7 DNA polymerase, *E. coli* DNA polymerase I F762Y, and Taq DNA polymerase F667Y, 0.02 µM to 1 µM, and T7 DNA polymerase Y526F, *E. coli* DNA polymerase I and Taq DNA polymerase F667Y, 100 to 2,000 µM. The reactions were carried out and the samples were analyzed by denaturing polyacrylamide gel electrophoresis as described in Example 1. Drying of the gel, autoradiography, and Phosphoimager analysis were as described in Example 1. The Table below summarizes the results from this experiment; the values shown for T7 DNA polymerase, *E. coli* DNA polymerase I F762Y, and Taq DNA polymerase F667Y are the absolute ratios obtained in Example 6 by statistical analysis of the rate of exponential decay in intensity of dideoxy-terminated fragments obtained using a 1:1 ratio of dNTPs to ddNTPs. The values obtained for T7 DNA polymerase Y526F, *E. coli* DNA polymerase I and Taq DNA polymerase were obtained by determining the ratios of ddNTP to dNTP required to generate a series of dideoxy-terminated fragments of comparable average length to a series generated using T7 DNA polymerase, *E. coli* DNA polymerase I F762Y, and Taq DNA polymerase F667Y, respectively; i.e., for each pair of wild-type and mutant DNA polymerases the ratios of ddNTPs-:dNTPs were determined that give a comparable distribution of dideoxy-terminated fragments. The ddNTP:dNTP ratio used in the reaction with the strongly discriminating enzyme (i.e. the one that contains phenylalanine at the critical position) divided by the ddNTP:dNTP ratio used to obtain a comparable distribution of dideoxy-terminated fragments with the relatively non-discriminating enzyme (i.e. the one that contains tyrosine at the critical position) gives a factor that corresponds to the difference in efficiency between the two DNA polymerases in their use of ddNTPs relative to the comparable dNTP. This factor was multiplied by the absolute ratios obtained for T7 DNA polymerase, *E. coli* DNA polymerase I F762Y, and Taq DNA polymerase F667Y in Example 1 in order to obtain the values shown below for T7 DNA polymerase Y526F, *E. coli* DNA polymerase I and Taq DNA polymerase, respectively.

| | Polymerase Incorporation Rate Ratios | | | |
|---|---|---|---|---|
| | dG/ddG | dA/ddA | dT/ddT | dC/ddC |
| T7 DNA polymerase | 3.2 | 3.3 | 2.8 | 3.7 |
| T7 DNA polymerase Y526F | 6,400 | 7,300 | 8,400 | 11,000 |
| E. coli DNA polymerase I | 140 | 720 | 1,100 | 250 |
| E. coli DNA polymerase I F762Y | 0.56 | 0.72 | 0.54 | 0.75 |
| Taq DNA polymerase | 1,400 | 4,700 | 4,500 | 2,600 |
| Taq DNA polymerase F667Y | 0.45 | 0.59 | 0.56 | 0.32 |

The table below summarizes the effect of having tyrosine in place of phenylalanine at the critical selectivity residue of T7 DNA polymerase, E. coli DNA polymerase I and Taq DNA polymerase on the use of ddNTPs relative to dNTPs.

| Polymerase | Residue | Average Rate dN/ddN | Improvement in Use of ddNTPs |
|---|---|---|---|
| T7 DNA polymerase | Tyrosine (WT) | 3.0 | 3,000 × |
| | Phenylalanine | 8,000 | |
| E. coli DNA polymerase I | Phenylalanine (WT) | 600 | |
| | Tyrosine | 0.6 | 1,000 × |
| Taq DNA polymerase | Phenylalanine (WT) | 3,000 | |
| | Tyrosine | 0.5 | 6,000 × |

To use this test to determine the extent of discrimination of a new DNA polymerase, reactions are carried out as described above initially using a wide range of ratios of ddNTPs to dNTPs, and comparing the distribution of dideoxy-terminated fragments on a denaturing polyacrylamide gel to those of a standard, e.g. T7 DNA polymerase. Matching the lanes that have comparable average lengths of DNA fragments, the ratio of ddNTPs:dNTPs of the new DNA polymerase is divided by the ratio used with T7 DNA polymerase to give the level of discrimination against ddNTPs by the new DNA polymerase relative to T7 DNA polymerase.

To use this test to determine whether the modification of a DNA polymerase results in a decrease in its ability to discriminate against ddNTPs (i.e., incorporate dideoxynucleotides more efficiently), an identical number of units of modified and unmodified DNA polymerases would be used in a series of reactions containing varying ratios of ddNTPs to dNTPs as described above. The average length of dideoxy-terminated fragments are compared for identical ratios of ddNTPs to dNTPs for the two enzymes. If the modification has resulted in a DNA polymerase that incorporates dideoxynucleotides more efficiently, the average length of dideoxy-terminated fragments will be shorter for reactions using the modified DNA polymerase compared with those using the unmodified DNA polymerase at the same ratios of ddNTP to dNTP, while the average length will be longer for reactions using the modified DNA polymerase if the modification resulted in a DNA polymerase that is more discriminatory towards ddNTPs.

This test can also be used to determine whether a modification of a DNA polymerase results in a decrease in its ability to discriminates against analogs of ddNTPs, for example fluorescently tagged ddNTPs. This is possible even if one does not know the concentration of the analogs being tested. As an example of this, we compared the ability of Taq DNA polymerase and Taq DNA polymerase F667Y to use each of the four DyeDeoxy Terminators manufactured by Applied Biosystems (part number 401150). These DyeDeoxy Terminators have four different fluorescent moieties covalently bound to each of the four ddNTPs (see Example 12 for more detail). For each of the DyeDeoxy Terminators, the ratio of dNTPs to DyeDeoxy Terminators was varied over a 16,000 fold range by intervals of two-fold, and the pattern of dideoxy-terminated fragments was compared on the autoradiograph to determine the ratios required for each of the two enzymes to obtain the same average length of dideoxy-terminated fragments. The Table below summarizes these results. For each Terminator, the column labeled "Ratio" represents the ratio of the ratios of ddNTP to DNTP required to give fragments of identical average length for Taq DNA polymerase versus Taq DNA polymerase F667Y. As with normal ddNTPs, Taq DNA polymerase F667Y incorporates the fluorescent ddNTP derivatives much more efficiently that does the unmodified Taq DNA polymerase, by at least a factor of 400.

| Dye Deoxy Terminator | Ratio |
|---|---|
| G Terminator | >400 |
| A Terminator | >2,000 |
| T Terminator | >2,000 |
| C Terminator | >2,000 |

As discussed previously, one complication that can arise in the use of this test is when the DNA polymerase being tested has an associated exonuclease activity. The problems that 5' to 3' and 3' to 5' exonucleases can cause and ways to minimize their effects when present are discussed in Example 1. When testing to determine whether the modification of a polymerase decreases its ability to incorporate dideoxynucleotides, one class of mutants that can have this effect are ones that inactivate a normally very active 3' to 5' exonuclease activity (see for example Tabor and Richardson 84, Proc. Natl. Acad. Sci. 4767, 1987). If one has a DNA polymerase that gives an apparent increase in the ability of the DNA polymerase to incorporate dideoxynucleotides, and one wants to determine whether it is in the polymerase domain or the exonuclease domain, it is necessary to carry out an exonuclease assay on the enzyme; a mutation that affects primarily the exonuclease activity of the enzyme will have a greater effect on the exonuclease activity of the enzyme than on the polymerase activity. Preferably, one would measure the exonuclease activity on a DNA substrate labeled at its 3' end with $^{32}$P-ddAMP. As in Example 1, it is important to inhibit pyrophosphorolysis in these reactions in order to avoid it increasing the apparent discrimination against ddNTPs by a DNA polymerase. This is readily accomplished by including pyrophosphatase in the reaction.

Example 3. Determination of the efficiency of incorporation of dideoxynucleotides by inhibition of DNA synthesis on a single-stranded M13 DNA—unlabeled 40-mer primer complex In this example the sensitivity of a DNA polymerase to a ddNTP is determined by measuring the ability of varying concentrations of the ddNTP to inhibit a standard DNA synthesis reaction. The DNA synthesis assay is a modification of that described in Tabor and Richardson 264 J. Biol. Chem. 6447, 1989. The standard 40 mer primer is annealed to the M13 mGP1-2 single-stranded DNA template in a reaction mixture (1X=25 µl) containing 2 µg of M13 mGP1-2 DNA, 6 pmoles of primer (a 10-fold molar excess to template), 40 mM Tris.HCl, pH 8.0, 10 mM $MgCl_2$ and 100 mM NaCl. The mixture is incubated 65° C. for 2 min and then cooled to room temperature over 30 min. The standard reaction mixture (45 µl) contained 22 mM Tris.HCl, pH 8.0, 5.5 mM $MgCl_2$, 55 mM NaCl, 300 µM dGTP, dATP, dCTP and [$^3$H]TTP (30 cpm/pmol), and varying concentrations of one of the four or all four ddNTPs. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 5 µl aliquots of dilutions (0.01 to 1 unit) of the DNA polymerase being analyzed, diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are terminated by the addition of 5 µl of 100 mM EDTA, and 45 µl is spotted onto Whatman DE81 filter discs. The discs are washed in 4 changes of 150 ml of 0.3M ammonium formate, p H 8.0, followed by 2 changes of 150 ml of 90% ethanol, each of 5–10 min duration. The disks are then dried under a heat lamp and counted in a scintillation counter in the presence of 5 ml of fluor (Opti-Fluor O, Packard). From the amount of radioactivity on each disk, the amount of total DNA synthesis is calculated.

Specific DNA polymerases being tested may have optimum buffer, pH, salt, or temperature conditions that differ from those suggested above. Each DNA polymerase should be tested under the conditions that give optimum specific polymerase activity for that enzyme.

To determine whether a given DNA polymerase discriminates against dideoxynucleotides, first a series of reactions are carried out in the absence of ddNTPs, varying the DNA polymerase concentration to determine the range where the activity varies approximately linearly with enzyme concentration for both the modified and unmodified forms of the enzyme. An enzyme concentration is chosen that is in this linear range for both forms of the enzyme; e.g., an enzyme concentration whereby about 30% of the template is replicated in the 10 min reaction is likely to be in such a linear range.

Once a proper enzyme concentration is chosen, a series of reactions are carried out varying the amount of either one ddNTP or preferably all four ddNTPs in the mixture, in order to determine the concentration required to inhibit 50% of the DNA synthesis. For example, under the conditions stated above (300 µM 4dNTPs), the following concentrations of a mixture of 4 ddNTPs are required to inhibit 50% of the DNA synthesis for the following six DNA polymerases:

| Polymerase | \|4ddNTP\| for 50% inhibition |
|---|---|
| T7 DNA polymerase | 0.1 µM |
| T7 DNA polymerase Y526F | 300 µM |
| *E. coli* DNA polymerase I | 20 µM |
| *E. coli* DNA polymerase I F762Y | 0.04 µM |
| Taq DNA polymerase | 150 µM |
| Taq DNA polymerase F667Y | 0.4 µM |

This test can be used to determine if a DNA polymerase discriminates against ddNTPs; if it does discriminate, then a higher concentration of 4ddNTPs will be required to inhibit 50% of the DNA synthesis in the assay described above.

Example 4. Determination of the efficiency of incorporation of dideoxynucleotides by measuring the incorporation of [α-$^{32}$P]dAMP into synthetic primer-template complexes In this example the competition between a dNTP and a ddNTP is assayed for use at a single site in a synthetic primer-template. This assay differs from the others in that it limits the comparison of the use of the two substrates to a single site, avoiding the complication of sequence-specific variability in discrimination. While this relatively simple assay is suitable for a preliminary screen of DNA polymerases for their ability to discriminate against ddNTPs, it should not be used to the exclusion of the assays presented in Examples 1–3 since often the discrimination against ddNTPs is strongly influenced by the neighboring sequences, an important problem for DNA sequence analysis (see for example Tabor and Richardson 265 *J. Biol. Chem.* 8322, 1990).

The two primer-templates shown below are used in this example. The first is used to determine the discrimination between dATP versus ddATP, while the second is used to determine the discrimination between dCTP versus ddCTP, dTTP versus ddTTP, and dGTP versus ddGTP.

Primer-Template A:

| 5' GGCGACGTTGTAAAACGACGGCCAGTGCCA | 3' (SEQ. ID. NO.17) |
| 3'    GCTGCAACATTTTGCTGCCGGTCACGGTTCCCC | 5' (SEQ. ID. NO.18) |

Primer-Template B:

| 5' GGCGACGTTGTAAAACGACGGCCAGTGCCA | 3' (SEQ. ID. NO.19) |
| 3'    GCTGCAACATTTTGCTGCCGGTCACGGTCAGTTTT | 5' (SEQ. ID. NO.20) |

Each reaction mixture contains 25 pmoles each of primer and template. The primer and template are mixed together and annealed in a reaction mixture (1X=10 µl) containing 40 mM Tris.HCl, pH 8.0, 10 mM $MgCl_2$ and 100 mM NaCl. The mixture is incubated 65° C. for 2 min and then cooled to room temperature (20°–25° C.) over 30 min. The standard reaction mixture (45 µl) for reactions carried out with Primer-Template A contains 22 mM Tris.HCl, pH 8.0, 5.5 mM $MgCl_2$, 55 mM NaCl, 25 pmoles of the Primer-Template A complex, 5 µM [α-$^{32}$P]dGTP (4,000 cpm/pmole) and varying concentrations of dATP and ddATP. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 5 μl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are terminated by the addition of 5 μl of 100 mM EDTA, and 45 μl is spotted onto Whatman DE81 filter discs. The discs are washed in 4 changes of 150 ml of 0.3M ammonium formate, pH 8.0, followed by 2 changes of 150 ml of 90% ethanol, each of 5–10 min duration. The disks are then dried under a heat lamp and counted in a scintillation counter in 5 ml of fluor (Opti-Fluor O, Packard). From the amount of radioactivity on each disk, the amount [$^{32}$P]dGMP incorporated was determined. The assumption is made once a single dAMP residue has been incorporated to remove the block for the incorporation of dGMP residues, four [$^{32}$P]dGMPs will be incorporated into each primer, and thus the number of dAMPs incorporated are one fourth the number of dGMPs incorporated.

All reactions are carried out with a constant amount of the DNA polymerase being analyzed; the amount of DNA polymerase should be sufficient to replicate 50% of the total dCMP residues in the single-stranded region of the template in the 10 min incubation in the presence of 10 μM DATP and the absence of ddATP. Specific DNA polymerases being tested may have optimum buffer, pH, salt, or temperature conditions that differ from those suggested above. Each DNA polymerase should be tested under the conditions that give optimum specific polymerase activity for that enzyme. Control reactions should also be carried out in which neither dATP nor ddATP are present; this defines the background DNA synthesis that should be subtracted from each sample. In general this is less than 10% of the DNA synthesis obtained when dATP is present.

Reactions are then carried out with 10 μM dATP and varying concentrations of ddATP, to determine the amount of ddATP required to inhibit DNA synthesis by 50%. Examples are shown in the Table below for the concentration of ddATP required to inhibit 50% of the DNA synthesis in the presence of 10 μM dATP. The polymerases are defined as in Example 1.

| Polymerase | [ddATP] for 50% inhibition |
| --- | --- |
| T7 DNA polymerase | ~30 μM |
| T7 DNA polymerase Y526F | >500 μM |
| E. coli DNA polymerase I | >500 μM |
| E. coli DNA polymerase I F762Y | ~6 μM |
| Taq DNA polymerase | >500 μM |
| Taq DNA polymerase F667Y | ~5 μM |

In order to carry out an analogous test measuring the discrimination against ddGTP, ddTTP or ddCTP, reactions are carried out identical to that described above except that Primer-Template B is used instead of Primer-Template A, and the reactions containing 10 μM dGTP, dTTP and dCTP and 5 μM [α-$^{32}$P]dATP (4,000 cpm/pmole) and varying concentrations of either ddGTP, ddTTP or ddCTP.

As with the other examples, DNA polymerases with a 3' to 5' exonuclease activity can interfere with this assay, making an enzyme more discriminatory against ddNTPs than that due to discrimination at the level of incorporation of the analog. In addition, enzymes with high levels of exonuclease activity can use up all the dNTPs in the reaction mixture (especially with the relatively low level of dNTPs present in these reactions), resulting in no net DNA synthesis (e.g. the native T7 DNA polymerase, see Tabor and Richardson 264 *J. Biol. Chem.* 6447, 1989). In these cases the concentration of DNA polymerase and the incubation time of the reaction should be adjusted to obtain the maximum level of DNA synthesis in the absence of ddNTPs.

Example 5. Determination of the efficiency of incorporation [α-$^{32}$P]ddNMPs into a synthetic primer-template complex In this example the competition between a dNMP and a ddNMP is assayed for incorporation at a single site in a synthetic primer-template. This assay differs from that in Example 4 in that the label is in [α-$^{32}$P]ddATP, and thus the incorporation of ddAMP is being measured. This assay can be used to test whether a ddNTP is inhibiting a DNA polymerase by acting as a chain terminator, being incorporated into the 3' end of the primer, or simply by binding the DNA polymerase and preventing further DNA synthesis without actually being incorporated into the primer.

In the example below the incorporation of ddAMP is measured using [α-$^{32}$P]ddATP and Primer-Template A (Example 4):

| Primer-Template A: | | |
| --- | --- | --- |
| 5' GGCGACGTTGTAAAACGACGGCCAGTGCCA | | 3' (SEQ. ID. NO.17) |
| 3'     GCTGCAACATTTTGCTGCCGGTCACGGTTCCCC | | 5' (SEQ. ID. NO.18) |

Incorporation of [α-$^{32}$P]ddGMP, [α-$^{32}$P]ddCMP and [α-$^{32}$P]ddTMP could be similarly tested on the appropriate template (for example, Primer-Template B in Example 4).

Each reaction mixture contains 25 pmoles each of primer and template (Primer-Template A, see above). The primer and template are mixed together and annealed in a reaction mixture (1X=10 μl) containing 40 mM Tris.HCl, pH 8.0, 10 mM MgCl$_2$ and 100 mM NaCl. The mixture is incubated 65° C. for 2 min and then cooled to room temperature over 30 min. The standard reaction mixture (45 μl) contains 22 mM Tris.HCl, pH 8.0, 5.5 mM MgCl$_2$, 55 mM NaCl, 25 pmoles of the Primer-Template A complex, 2.5M [α-$^{32}$P]ddATP (Amersham PB10235, >5000 Ci/mmol diluted with cold ddATP to a specific activity of 4,000 cpm/pmole) and varying concentrations of dATP. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 5 μl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are terminated by the addition of 5 μl of 100 mM EDTA, and 45 μl is spotted onto Whatman DE81 filter discs. The discs are washed in 4 changes of 150 ml of 0.3M ammonium formate, p H 8.0, followed by 2 changes of 150 ml of 90% ethanol, each of 5–10 min duration. The disks are then dried under a heat lamp and counted in a scintillation counter 5 ml of fluor (Opti-Fluor O, Packard). From the amount of radioactivity on each disk, the amount [$^{32}$P] ddAMP incorporated is determined.

All reactions are carried out with a constant amount of the DNA polymerase being tested; the amount of DNA polymerase should be that concentration which gives the highest level of incorporation of [$^{32}$P]ddAMP into Primer-Template A in the 10 min incubation in the absence of dATP. Specific DNA polymerases being tested may have optimum buffer, pH, salt, or temperature conditions that differ from those suggested above. Each DNA polymerase should be tested under the conditions that give optimum specific polymerase activity for that enzyme.

In order to use this assay to determine the level of discrimination against a ddNTP, reactions are carried out with a constant amount of the DNA polymerase and [$^{32}$P] ddATP, in the presence or absence of 2.5 µM dATP (an equimolar concentration to [$^{32}$P]ddATP) and the effect the presence of dATP has on the incorporation of [$^{32}$P]ddAMP is determined. If a DNA polymerase does not discriminate between the incorporation of ddAMP and dAMP, and it has no 3' to 5' exonuclease activity, then the addition of DATP will inhibit incorporation of [$^{32}$P]ddAMP by 50%.

This test is best for a DNA polymerase that efficiently incorporates ddNMPs, such as Taq DNA polymerase F667Y. For DNA polymerases that discriminate strongly against ddNMPs, the previous assay is preferred, in which the label is in a dNTP other than the one being used in competition with the ddNTP, since in that case much higher concentrations of the ddNTP can be used. However, with DNA polymerases that discriminate strongly against ddNMPs, if one is interested in testing whether a given mutation is reducing the level of discrimination against ddNMPs, this assay could be used by assaying the unmodified DNA polymerase on this substrate in the absence of DATP (measuring the incorporation of [$^{32}$P]ddAMP as a function of DNA polymerase concentration), and comparing the rate of incorporation to that of the mutant enzyme. If the mutation is reducing the discrimination against ddATP, then the mutant enzyme should have a higher specific activity for incorporation of [$^{32}$P]ddAMP.

As with the other examples, DNA polymerases with a 3' to 5' exonuclease activity can interfere with this assay, making an enzyme more discriminatory against ddNTPs than that due to discrimination at the level of incorporation of the analog. And as in Example 9, enzymes with high levels of exonuclease activity can deplete all the dNTPs, resulting in no net incorporation of [$^{32}$P]ddAMP. In these cases the concentration of DNA polymerase and the incubation time of the reaction should be adjusted to obtain the maximum level of incorporation of [$^{32}$P]ddAMP by the DNA polymerase being tested.

All of the above methods are based on radioactivity to detect either the length of the extended primer or the amount of DNA synthesis on the primer. The efficiency of incorporation of dideoxynucleotides by a DNA polymerase can also be measured nonradioactively. Two examples are presented below that make use of either fluorescent primers or fluorescent dye-dideoxy terminators that are detected on an Applied Biosystems Model 373A DNA Sequencing System.

Example 6. Determination of the efficiency of incorporation of dideoxynucleotides using a fluorescent primer annealed to single-stranded DNA and gel electrophoresis In this example a fluorescently labeled primer is annealed to single-stranded DNA and DNA synthesis reactions are carried out using varying ratios of dNTPs to ddNTPs. The samples are then loaded onto an Applied Biosystems Model 373A DNA Sequencing System, and the length of each fluorescent fragment is determined by direct fluorescent detection during gel electrophoresis. Reactions are carried out as described in Tabor and Richardson 265 *J. Biol. Chem.* 8322, 1990. The fluorescent primer used is "Fam" primer (Applied Biosystems). The DNA used is single-stranded M13 mGP1-2 DNA as described above. The primer is annealed to the M13 mGP1-2 single-stranded DNA template in a reaction mixture (1X=10 µl) containing 2 µg of M13 mGP1-2 DNA, 5 ng of primer, 40 mM Tris.HCl, pH 8.0, 10 mM MgCl$_2$ and 100 mM NaCl. The mixture is incubated 65° C. for 2 min and then cooled to room temperature over 30 min. The standard reaction mixture (18 µl) contains 22 mM Tris.HCl, pH 8.0, 5.5 mM MgCl$_2$, 55 mM NaCl, and varying concentrations of the 4dNTPs and one of the four ddNTPs. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 2 µl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are by the addition of 8 µl of 20 mM DTPA, 1M potassium acetate, pH 5.0, and 60 µl of ethanol. After centrifugation, the DNA is resuspended in 6 µl of 80% formamide, 10 mM Tris.HCl, pH 8.0, and 1 mM EDTA, and heated at 80° C. for 2 min immediately prior to loading on the polyacrylamide gel on the Applied Biosystems 373A DNA Sequencing System following the manufacturer's procedures.

Specific DNA polymerases being tested may have optimum buffer, pH, salt, or temperature conditions that differ from those suggested above. Each DNA polymerase should be tested under the conditions that give optimum specific polymerase activity for that enzyme. The concentration of DNA polymerase should be sufficient to extend most of the primers at least several hundred nucleotides or until a dideoxynucleotide has been incorporated in the 10 min reaction.

The ratio of dNTPs to ddNTPs is adjusted to obtain optimum peak intensities for approximately three hundred bases. For example, for Taq DNA polymerase approximately 10 µM 4dNTPs and 200–600 µM ddNTPs is optimal, while for Taq DNA polymerase F667Y approximately 300 µM 4dNTPs and 0.5–5 µM ddNTPs is optimal.

To determine whether a given DNA polymerase discriminates against dideoxynucleotides, reactions should be carried out at varying ratios of dNTPs to ddNTPs for the DNA polymerases, and the intensities of dideoxy-terminated fragments of different lengths are compared to determine whether the DNA polymerase is using ddNTPs more efficiently than a comparison enzyme.

Example 7. Determination of the efficiency of incorporation of fluorescent dideoxynucleotides by gel electrophoresis In this example a nonfluorescent primer is annealed to single-stranded DNA and DNA synthesis reactions are carried out using varying ratios of dNTPs to a single fluorescently labeled-ddNTP. The samples are then loaded onto an Applied Biosystems Model 373A DNA Sequencing System, and the length of each fluorescent fragment is determined by direct fluorescent detection during gel electrophoresis. The primer used in this example is the standard 40-mer, and the template is single-stranded M13 mGP1-2. The primer is annealed to the M13 mGP1-2 single-stranded DNA template in a reaction mixture (1X=10 μl) containing 2 μg of M13 mGP1-2 DNA, 6 pmoles of primer (a 10-fold molar excess to template), 40 mM Tris.HCl, pH 8.0, 10 mM MgCl$_2$ and 100 mM NaCl. The mixture is incubated 65° C. for 2 min and then cooled to room temperature over 30 min. The standard reaction mixture (18 μl) contains 22 mM Tris.HCl, pH 8.0, 5.5 mM MgCl$_2$, 55 mM NaCl, and varying concentrations of the 4dNTPs plus one of the four fluorescently-labeled ddNTPs. The four fluorescently labeled ddNTPs are from Applied Biosystems (Taq DyeDeoxy Terminator Cycle Sequencing Kit, part number 401150), and are referred to as G, A, T or C "DyeDeoxy Terminators" (manual for Taq DyeDeoxy Terminator Cycle Sequencing Kit, part number 901497, Rev. E). The reaction mixtures also contained 10 ng of yeast inorganic pyrophosphatase to inhibit pyrophosphorolysis that could otherwise increase the apparent discrimination by the DNA polymerase (Tabor and Richardson 265 J. Biol. Chem. 8322, 1990). The mixtures are incubated at 37° C. for 1 min (70° C. for thermophilic DNA polymerases), and the reactions are initiated by the addition of 2 μl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are by the addition of 8 μl of 20 mM EDTA, 1M potassium acetate, pH 5.0, and 60 μl of ethanol. After centrifugation, the DNA is resuspended in 6 μl of 80% formamide, 10 mM Tris.HCl, pH 8.0, and 1 mM DTPA, and heated at 80° C. for 2 min immediately prior to loading on the polyacrylamide gel on the Applied Biosystems 373A DNA Sequencing System following the manufacturer's procedures.

Specific DNA polymerases being tested may have optimum buffer, pH, salt, or temperature conditions that differ from those suggested above. Each DNA polymerase should be tested under the conditions that give optimum specific polymerase activity for that enzyme. The concentration of DNA polymerase used in these reactions should be that concentration that is sufficient to extend most of the primers at least several hundred nucleotides or until a dideoxynucleotide has been incorporated in the 10 min reaction. For DNA polymerases that have a 5' to 3' exonuclease activity, such as Taq DNA polymerase, the DNA polymerase concentration must be kept low enough to avoid this activity degrading a significant percentage of the 5' ends of the fragments.

To determine whether a DNA polymerase discriminates strongly or weakly against a fluorescent ddNTP, reactions are carried out using 20 μM 4dNTPs and 0.01 μl of each DyeDeoxy Terminator provided by Applied Biosystems (part number 401150). When Taq DNA polymerase is used under these conditions, most of the fluorescence is either in unincorporated dye-ddNTPs at the leading front of the gel, or in fragments greater than several hundred bases in length. In contrast, with the Taq DNA polymerase mutant F667Y, under these conditions most of the fluorescence is in fragments that are less than several hundred bases in length, and a significantly lower percentage of the total fluorescence is in unincorporated dye-ddNTPs at the leading front of the gel.

To determine whether a given DNA polymerase discriminates against dideoxynucleotides, reactions are carried out at varying ratios of dNTPs to DyeDeoxy Terminators for the DNA polymerase, and the average length of the resulting fluorescent fragments are compared to determine whether the DNA polymerase is using the DyeDeoxy Terminators more efficiently than a comparison enzyme.

The following examples provide tests for determining the uniformity of band intensities produced from dideoxy-terminated fragments synthesized by different DNA polymerases.

Example 8. Determination of uniformity of incorporation of dideoxynucleotides using a single-stranded M13 DNA—5' $^{32}$P-labeled 40-mer primer complex and gel electrophoresis In this example the uniformity of dideoxynucleotide incorporation is measured on a 5' $^{32}$P-end labeled primer extended on a single-stranded M13 DNA template. Such uniformity is a measure of non-discriminatory properties of a DNA polymerase. Three activities can cause variability in band intensity of dideoxy-terminated fragments. One is exonuclease activity that can preferentially at some sequences; this is avoided by removal of the activity selectively either by chemical or genetic means (see for example Tabor and Richardson 264, J. Biol. Chem. 6447, 1989). The second is pyrophosphorolysis; this is readily avoided by including pyrophosphatase in the reaction mixture, which degrades the pyrophosphate that accumulates during DNA synthesis and is a necessary substrate for pyrophosphorolysis. The third is sequence-specific variability in the incorporation of dideoxynucleotides. Variability in band intensity is detrimental to DNA sequence analysis, decreasing the accuracy of the DNA sequence determined. This test is designed to compare the degree of variability in band intensities in fragments synthesized by different DNA polymerases, including DNA polymerases that may incorporate dideoxynucleotides more efficiently.

The primer, template and reaction conditions in this Example are identical to that described in Examples 1 and 2. The template is M13 mGP1-2 single-stranded DNA described, and the primer is the standard 40 mer. Reaction conditions used are those that are optimum for the DNA polymerase being tested with regard to buffer, pH, salts, and temperature of the reaction. It is preferred that magnesium is the only metal ion present in the reaction mixture (i.e., the reactions are carried out in the absence of added manganese ions). A concentration of DNA polymerase is chosen whereby most of the primers are extended in a 10 min reaction and are terminated by the incorporation of a dideoxynucleotide. The ratios of dNTPs to ddNTPs are adjusted for the specific DNA polymerase being tested so that the average fragment size is approximately 100–300 nucleotides. ddCTP is the preferred ddNTP to use for the test of uniformity since fragments terminated with this dideoxynucleotide tend to have the most variability in intensities (see for example Tabor and Richardson 86 Proc. Natl. Acad. Sci. 4076, 1989). Gel electrophoresis, autoradiography, and analysis of the band intensities by either scanning of the gel or phosphoimager analysis are as described in Example 1. Electrophoresis is carried out until fragments of approximately 55 nucleotides in length are at the bottom of the gel (the dye bromphenol blue has run off the bottom of the gel and the dye xylene cyanol is approximately 8 cm from the bottom of the gel).

For a given series of ddNMP-terminated fragments, for example a series of ddCMP-terminated fragments, the intensities of the first 20 fragments from the bottom of the gel are determined, preferably by Phosphoimager analysis. Alternatively, the autoradiograph can be scanned by an imaging densitometer to determine the relative intensities of the first 20 fragments. These intensities are then analyzed statistically as described in Example 1 in order to determine their variability. For example, the values can be plotted using the Macintosh program Kaleidograph Version 3.0 (Synergy Software). The resulting plots are fit to an exponential decay curve using the Kaleidograph library routine for this function. $R^2$, the correlation index for the data, is calculated by the Kaleidograph library routine. This is a measure of the variability in band intensities. The values obtained for $R^2$ using a new DNA polymerase are compared to those obtained using known DNA polymerases, for example A28 T7 DNA polymerase (Sequenase Version 2.0, United States Biochemical Corporation) in the presence of magnesium or manganese (see Tabor and Richardson 265 *J. Biol. Chem.* 8322, 1990), *E. coli* DNA polymerase I (either Klenow fragment or Klenow fragment with the mutation F762Y) or Taq DNA polymerase (either wild-type or the mutant F667Y). The $R^2$ values obtained with these known DNA polymerases are used as standards by which to compare a new DNA polymerase for its uniformity.

Example 9. Determination of uniformity of incorporation of [α-$^{32}$P]ddNMPs using a single-stranded M13 DNA—unlabeled primer complex and gel electrophoresis In this example the uniformity of dideoxynucleotide incorporation is measured using an unlabeled primer annealed to a single-stranded M13 DNA template and carrying out DNA synthesis in the presence of [α-$^{32}$P]ddATP. The test described in Example 8 is preferred over this one for measuring uniformity of dideoxynucleotide-terminated fragments, since it is more amenable to use of high concentrations of ddNTPs, which are required for use in enzymes that discriminate strongly against ddNTPs, such as *E. coli* DNA polymerase I, Taq DNA polymerase and T7 DNA polymerase Y526F. The test in this example is most suited for use with enzymes that incorporate dideoxynucleotides efficiently, such as T7 DNA polymerase, *E. coli* DNA polymerase I F762Y and Taq DNA polymerase F667Y.

The primer, template and general reaction conditions in this example are similar to those described in Example 3, with the following exceptions. Reaction conditions used are those that are optimum for the DNA polymerase being tested with regard to buffer, pH, salts, and temperature of the reaction. It is preferred that magnesium is the only metal ion present in the reaction mixture (i.e. the reactions are carried out in the absence of added manganese ions). The reactions are carried out with 50 μM dGTP, dCTP and dTTP, and varying concentrations of DATP and [α-$^{32}$P]ddATP. The concentrations of DATP and [α-32P]ddATP are chosen to maximize the amount of radioactivity in fragments approximately 100 nucleotides in length. All other aspects with respect to gel electrophoresis and analysis of the radioactive fragments are as described in Example 8.

Example 10. Determination of uniformity of incorporation of dideoxynucleotides using a single-stranded M13 DNA—fluorescently-labeled primer complex and gel electrophoresis In this example, reactions are carried out as described in Example 6. The template is M13 mGP1-2 single-stranded DNA, and the primer is the standard 40 mer. Reaction conditions used are those that are optimum for the DNA polymerase being tested with regard to buffer, pH, salts, and temperature of the reaction. It is preferred that magnesium is the only metal ion present in the reaction mixture (i.e., the reactions are carried out in the absence of added manganese ions). A concentration of DNA polymerase is chosen whereby most of the primers are extended in a 10 min reaction and are terminated by the incorporation of a dideoxynucleotide. The ratios of dNTPs to ddNTPs are adjusted for the specific DNA polymerase being tested so that the average fragment size is approximately 100–200 nucleotides. ddCTP is the preferred ddNTP to use since fragments terminated with this dideoxynucleotide tend to have the most variability in intensities (see for example Tabor and Richardson 86 *Proc. Natl. Acad. Sci.* 4076, 1989). The intensities of up to the first 50 dideoxy-terminated fragments from the primer (approximately 200 nucleotides) are determined, and they are analyzed statistically as described in Example 8. The correlation index $R^2$ is determined for the DNA polymerase being tested, and compared with that obtained with known DNA polymerases such as those described in Example 8. Alternatively, the heights of the first 50 bands are determined and the ratio of heights of adjacent bands are calculated and used as a measure of variability; the maximum and mean of these ratios obtained from reactions carried out with the DNA polymerase being tested are compared with the values obtained for reactions carried out using known DNA polymerases such as those described in Example 8.

Example 11. Determination of uniformity of incorporation of fluorescent dideoxynucleotides by gel electrophoresis In this example, reactions are carried out as described in Example 7. In order to determine the uniformity of incorporation of the DyeDeoxy Terminators for a specific DNA polymerase, the concentration of dNTPs and the specific DyeDeoxy Terminator are chosen to obtain fluorescently labeled fragments that average 100–200 nucleotides in length. The intensity of fluorescence is determined for fragments 10 to 40 from the primer (the first 10 fragments near the fluorescently labeled primer are ignored). The fragments are analyzed statistically as described in Example 8, and the average variability is defined by $R^2$, the correlation index for the data fitted to an exponential decay curve. The values obtained for $R^2$ are compared with those obtained using known DNA polymerases as described in Example 8. To determine if a specific mutation in a DNA polymerase is resulting in that DNA polymerase producing bands that have less variability, the $R^2$ value obtained for the mutant DNA polymerase is compared to that obtained for the unmodified DNA polymerase.

Pharmaceutical Formulations and Modes of Administration

The particular nucleoside or analog thereof that affects the disorder of interest can be administered to a patient or plant either by itself, or in a pharmaceutical composition where it is mixed with a suitable carrier(s) or excipient(s). In treating a patient exhibiting a disorder of interest, a therapeutically effective amount of an agent or agents such as these is administered. A therapeutically effective dose refers to that amount of the compound that results in amelioration of one or more symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

As noted above, the analogs of this invention may be used with other useful agents, such as antibiotics already used in treatment of disease. Such agents can be coformulated as desired.

Identification of Analogs

Non-discriminating DNA polymerases may be used to screen for additional analogs as discussed above. That is, those polymerases can be used in standard DNA synthesis methods to observe incorporation of a test agent. If the agent is incorporated at a greater rate than by a discriminatory DNA polymerase it is potentially useful in this invention. The assays described above can be used for these assays by simply substituting the test agent for a ddNTP.

By "screening" is meant investigating an agent for the presence or absence of a property. The process includes measuring and detecting various properties, including the level of DNA polymerase activity or binding with an agent. Depending upon the type of interaction present, various methods may be used to measure the level of interaction. For example, the strengths of covalent bonds are often measured in terms of the energy required to break a certain number of bonds (i.e., kcal/mol). Non-covalent interactions are often described as above and also in terms of the distance between the interacting molecules.

Such compounds may include, but are not limited to, small organic molecules, synthetic compounds, natural products, and other sources of potentially biologically active materials which may be screened as described herein. Thus, any compound active at a non-discriminating DNA polymerase but not at a discriminating DNA polymerase is particularly useful in this invention and can be determined by routine screening.

Agents capable of inhibiting DNA polymerase activity mainly in non-discriminating DNA polymerases can be identified. A sufficient amount of such an agent or agents may be administered to a patient so that the target disease is reduced or eliminated.

Derivatives of Analogs

Also provided herein are functional derivatives of an analog, e.g., a "chemical derivative."

A "functional derivative" retains at least a portion of the function of the analog, i.e., reactivity with a non-discriminating DNA polymerase which permits its utility in accordance with the present invention.

A "chemical derivative" of the complex contains additional chemical moieties not normally a part of the analog. Covalent modifications of the analog are included within the scope of this invention. Such modifications may be introduced into the molecule by reacting targeted residues of the analogs with an organic derivatizing agent that is capable of reacting with selected atoms or molecules.

Such derivatized moieties may improve the stability, solubility, absorption, biological half life, and the like. The moieties may alternatively eliminate or attenuate any undesirable side effect of the analog. Moieties capable of mediating such effects are disclosed, for example, in Remington's Pharmaceutical Sciences, 18th ed., Mack Publishing Co., Easton, Pa. (1990).

Diagnosis

This invention also features diagnosis of the presence of an organism causative of a disease or condition.

By "disease or condition" is meant a state in an organism, e.g., a human or other animal or plant which is recognized as abnormal by members of the medical, veterinary, horticultural or agricultural community. The disease or condition is characterized by the presence of a non-discriminating DNA polymerase in a cell.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the disease or conditions. Thus, the detection of an important symptom, such as the detection of a non-discriminating DNA polymerase may form the basis to define and diagnose a disease or condition.

Such diagnosis can be performed as described above using standard methodologies. The detection of a non-discriminatory DNA polymerase distinct from those expected in a sample (e.g., in human tissue—a non-discriminating mitochondrial DNA polymerase or human β-DNA polymerase) is diagnostic of infection e.g., by a mycobacterium. Those in the art will recognize standard methods by which such testing can be used to readily distinguish different DNA polymerase so that the test is as specific as is necessary.

Other embodiments are within the following claims.

---

We claim:

1. Method for diagnosis of the presence of a mycobacterial organism potentially causative of a disease or condition in an animal or plant patient comprising the steps of:

providing a sample from said patient potentially containing said organism, detecting the presence in said sample of a non-discriminating DNA polymerase not normally present in said sample by determining the ability of said polymerase to incorporate dideoxynucleotides relative to deoxynucleotides, wherein the presence of said non-discriminating polymerase is diagnostic of the presence of said organism in said patient.

2. The method of claim 1, wherein said disease is leprosy.

3. The method of claim 1, wherein said disease is tuberculosis.

* * * * *